United States Patent [19]

Sasse et al.

[11] Patent Number: 4,806,540
[45] Date of Patent: Feb. 21, 1989

[54] 1-HETEROARYL-4-ARYL-PYRAZOLE MICROBICIDES

[75] Inventors: Klaus Sasse, Bergisch-Gladbach; Gerd Hänssler, Leverkusen; Hans-Georg Schmitt; Wilfried Paulus, both of Krefeld, all of Fed. Rep. of Germany

[73] Assignee: Bayer Aktiengesellschaft, Leverkusen, Fed. Rep. of Germany

[21] Appl. No.: 99,928

[22] Filed: Sep. 23, 1987

Related U.S. Application Data

[62] Division of Ser. No. 886,284, Jul. 15, 1986.

[30] Foreign Application Priority Data

Jul. 30, 1985 [DE] Fed. Rep. of Germany ....... 3527157

[51] Int. Cl.$^4$ ................. C07D 401/04; C07D 215/38; C07D 215/20; C07D 215/36; A61K 31/44; A61K 31/47; A61K 31/505
[52] U.S. Cl. .................................. 514/236.5; 546/271; 546/256; 546/279; 546/162; 546/170; 546/172; 546/171; 546/174; 546/175; 546/176; 546/177; 546/194; 514/339; 514/312; 514/313; 514/314; 514/318; 514/333; 514/341; 544/128; 544/131; 544/124
[58] Field of Search ............... 546/271, 256, 279, 162, 546/170, 172, 171, 174, 175, 176, 177, 194; 514/339, 312, 313, 314, 318, 333, 341, 230, 232, 234, 236, 237, 238, 240; 544/128, 131, 124

[56] References Cited

U.S. PATENT DOCUMENTS 4,689,331  8/1987  Ankner et al. .................. 546/271

Primary Examiner—John M. Ford
Assistant Examiner—Robert C. Whittenbaugh
Attorney, Agent, or Firm—Sprung Horn Kramer & Woods

[57] ABSTRACT

Novel microbicidally active 1-heteroaryl-4-aryl-pyrazole derivatives of the formulae (I) and/or (1A)

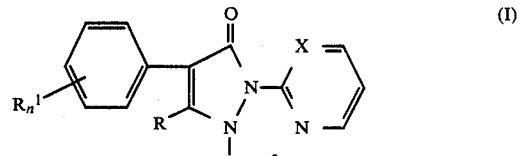

(I)

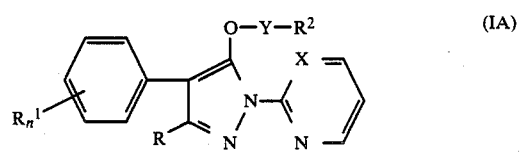

(IA)

in which
R represents hydrogen or alkyl,
$R^1$ represents halogen, hydroxyl, optionally substituted alkyl, optionally substituted alkoxy, a radical —S-(O)$_p$-alkyl which is optionally substituted in the alkyl part, nitro or optionally substituted amino, or represents a fused-on carbocyclic or heterocyclic radical
p represents the integer 0, 1 or 2,
n represents an integer from 0 to 5,
X represents =CH—, or represents a nitrogen atom,
Y represents CO or SO$_2$ and
$R^2$ represents hydrogen, in each case optionaly substituted alkyl, cycloalkyl or aryl or a heterocyclic radical, or represents OR$^3$, or also represents SR$^3$, if Y is CO,
wherein
$R^3$ represents optionally substituted alkyl or aryl, or
$R^2$ represents a radical

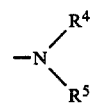

wherein
$R^4$ represents hydrogen or saturated or unsaturated optionally substituted alkyl and optionally substituted alkyl, optionally substituted cycloalkyl, optionally substituted aryl or an optionally substituted heterocyclic radical, or
$R^4$ and $R^5$, together with the nitrogen atom on which they are located, form a heterocyclic ring which optionally contains further hetero atoms and can optionally be mono- or polysubstituted by identical or different substituents.

7 Claims, No Drawings

1-HETEROARYL-4-ARYL-PYRAZOLE MICROBICIDES

This is a division of application Ser. No. 886,284 filed July 15, 1986 now pending.

The invention relates to new 1-heteroaryl-4-aryl-pyrazole derivatives, a process for their preparation and their use as microbicides.

It is already known that certain heterocyclic compounds, such as, for example, N-trichloromethylthiophthalimide and -tetrahydrophthalimide, have good fungicidal actions (compare U.S. Pat. Nos. 2,553,770, 2,553,771 and 2,553,776). Organic sulphur compounds, such as, for example, zinc ethylene-1,2-bis-(dithiocarbamate), furthermore are also compounds which have a good fungicidal action (compare, for example, R. Wegler "Chemie der Pflanzenschutz- und Schädlingsbekämpfungsmittel" ("Chemistry of Plant Protection Agents and Agents for Combating Pests"), Springer Verlag, Berlin, Heidelberg, New York 1970, Volume 2, page 65 et seq.). The action of these compounds cannot always be completely satisfactory in some fields of use under certain conditions, for example when low amounts and concentrations are applied.

1,4-Diaryl-pyrazolin-5-ones, which are used as herbicides, are furthermore known. Nothing is known of a fungicidal activity (compare DE-OS (German Published Specification) No. 2,651,008).

Furthermore, 1-heteroaryl-4-aryl-pyrazolin-5-ones, such as, for example, 1-pyrimid-2-yl-4-phenyl-pyrazolin-5-one, and their microbicidal properties are known from U.S. patent application Ser. No. 733,450, filed May 10, 1985, now pending.

New 1-heteroaryl-4-aryl-pyrazole derivatives of the formulae (I) and (IA)

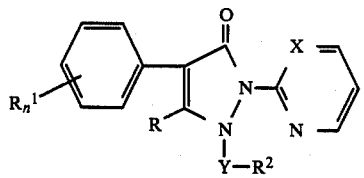
(I)

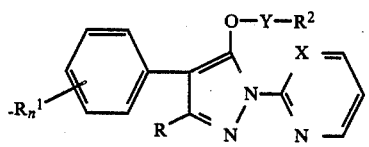
(IA)

in which

R represents hydrogen or alkyl, $R^1$ represents halogen, hydroxyl, optionally substituted alkyl, optionally substituted alkoxy, a radical —S-$(O)_p$-alkyl which is optionally substituted in the alkyl part, nitro or optionally substituted amino, or represents a fused-on carbocyclic or heterocyclic radical, p represents the integer 0, 1 or 2, n represents an integer from 0 to 5, X represents =CH—, or represents a nitrogen atom, Y represents CO or $SO_2$ and $R^2$ represents hydrogen, in each case optionally substituted alkyl, cycloalkyl or aryl or a heterocyclic radical, or represents $OR^3$, or also represents $SR^3$, if Y is CO, wherein $R^3$ represents optionally substituted alkyl or aryl, or $R^2$ represents a radical

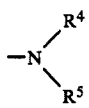

wherein $R^4$ represents hydrogen or saturated or unsaturated optionally substituted alkyl and $R^5$ represents hydrogen, saturated or unsaturated, optionally substituted alkyl, optionally substituted cycloalkyl, optionally substituted aryl or an optionally substituted heterocyclic radical, or $R^4$ and $R^5$, together with the nitrogen atom on which they are located, form a heterocyclic ring which optionally contains further hetero atoms and can optionally be mono- or polysubstituted by identical or different substituents.

It has furthermore been found that the new 1-heteroaryl-4-aryl pyrozole derivatives of the formulae (I) and (I.A)

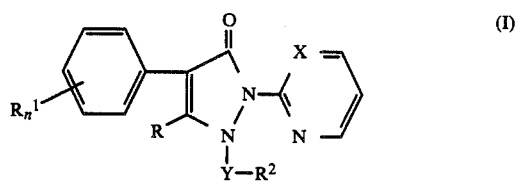
(I)

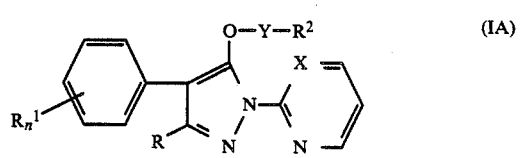
(IA)

in which

R represents hydrogen or alkyl, $R^1$ represents halogen, hydroxyl, optionally substituted alkyl, optionally substituted alkoxy, a radical —S-$(O)_p$-alkyl which is optionally substituted in the alkyl part, nitro or optionally substituted amino, or represents a fused-on carbocyclic or heterocyclic radical, p represents the integer 0, 1 or 2, n represents an integer from 0 to 5, X represents =CH—, or represents a nitrogen atom, Y represents CO or $SO_2$ and $R^2$ represents hydrogen, in each case optionally substituted alkyl, cycloalkyl or aryl or a heterocyclic radical, or represents $OR^3$, or also represents $SR^3$, if Y is CO, wherein $R^3$ represents optionally substituted alkyl or aryl, or $R^2$ represents a radical

wherein $R^4$ represents hydrogen or saturated or unsaturated optionally substituted alkyl and $R^5$ represents hydrogen, saturated or unsaturated, optionally substituted alkyl, optionally substituted cycloalkyl, optionally substituted aryl or an optionally substituted heterocyclic radical, or R⁴ and R⁵, together with the nitrogen atom on which they are located, form a heterocyclic ring which optionally contains further hetero atoms and can optionally be mono- or polysubstituted by identical or different substituents, are obtained by a process in which 1-heteroaryl-4-aryl-pyrazolin-5-ones of the formula (II) or (IIA)

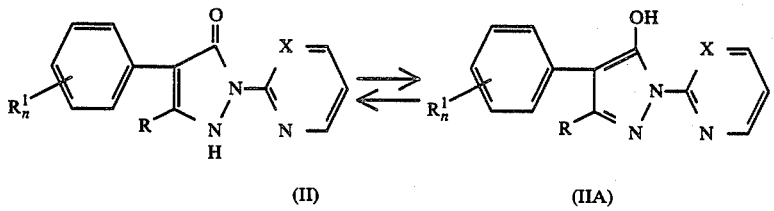

in which

R, $R^1$, X and n have the abovementioned meanings, are reacted with a reactive derivative of an acid of the formula (III)

in which $R^2$ and Y have the abovementioned meanings and

Z represents halogen, an acyloxy radical, a sulphonyloxy radical or an azole radical if appropriate in the presence of an acid-binding agent.

Finally, it has been found that the 1-heteroaryl-4-aryl-pyrazole derivatives of the formulae (I) and (IA) can be employed for combating microbial parasites.

Surprisingly, the compounds of the formulae (I) and (IA) according to the invention exhibit a more powerful antimicrobial activity than the active compounds already known from the prior art, such as, for example, N-trichloromethylthio-phthalimide or -tetrahydrophthalimide, zinc ethylene-1,2-bis-(dithiocarbamate) and/or N,N-dimethyl-N'-phenyl-N'-dichlorofluoro-methylthio-sulphamide. The compounds according to the invention thus represent an enrichment of the art.

Formula (I) or (IA) provides a general definition of the 1-heteroaryl-4-aryl-pyrazole derivatives according to the invention.

Preferred compounds of the formulae (I) and (IA) are those
in which

R represents hydrogen or alkyl with 1 to 4 carbon atoms, $R^1$ represents halogen, such as fluorine, chlorine, bromine and iodine, or hydroxyl, or represents alkyl with 1 to 4 carbon atoms, or represents halogenoalkyl with 1 or 2 carbon atoms and 1 to 5 identical or different halogen atoms, or represents alkoxy with 1 to 6 carbon atoms or halogenoalkoxy with 1 or 2 carbon atoms and 1 to 5 identical or different halogen atoms, or represents alkoxyalkoxy with 1 to 4 carbon atoms per alkyl part, or represents alkylthioalkoxy with 1 to 4 carbon atoms per alkyl part, or represents aryloxyalkoxy with 1 to 4 carbon atoms in the alkyl part and 6 to 10 carbon atoms in the aryl part, or represents alkylthio with 1 to 6 carbon atoms, or represents halogenoalkylthio with 1 or 2 carbon atoms and 1 to 5 identical or different halogen atoms, or represents alkoxyalkylthio with 1 to 4 carbon atoms per alkyl part, or represents alkylthioalkylthio with 1 to 4 carbon atoms per alkyl part, or represents alkylsulphinyl with 1 to 6 carbon atoms, or represents halogenoalkylsulphinyl with 1 or 2 carbon atoms and 1 to 5 identical or different halogen atoms, or represents alkoxyalkylsulphinyl or alkylthioalkylsulphinyl with 1 to 4 carbon atoms per alkyl part, or represents alkylsulphonyl with 1 to 6 carbon atoms, or represents halogenoalkylsulphonyl with 1 or 2 carbon atoms and 1 to 5 identical or different halogen atoms, or represents alkoxyalkylsulphonyl or alkylthioalkylsulphonyl with 1 to 4 carbon atoms per alkyl part, or represents nitro, amino, mono- or dialkylamino with 1 to 4 carbon atoms per alkyl part, or acylamino, or represents a fused-on five-membered or six-membered carbocyclic ring which can be interrupted once or several times by identical or different atoms from the group comprising oxygen, sulphur and nitrogen atoms, X represents =CH—, or represents a nitrogen atom, Y represents CO or SO₂ and n represents an integer from 0 to 3, and $R^2$ represents hydrogen or an alkyl radical which has 1–12 carbon atoms and can be substituted by one or more halogen atoms, by a hydroxyl group, by a radical —A—$R^6$, in which A represents oxygen, sulphur, SO or SO₂ and $R^6$ represents an optionally substituted aliphatic, aromatic or heterocyclic radical, or by the NO₂ group or by a group

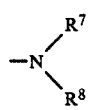

in which $R^7$ and $R^8$ independently of one another denote hydrogen, alkyl, aryl, a heterocyclic radical or an acyl group, or by the cyano group, a carboxylic acid ester radical or a carboxylic acid amide radical which is optionally substituted on the N atom, or by an optionally substituted aryl radical or an optionally substituted or fused heterocyclic radical, or $R^2$ represents cycloalkyl which has 3 to 8 ring carbon atoms and is optionally substituted by halogen, hydroxyl, alkoxy, aryloxy, alkyl or aryl or contains optionally fused-on rings, or $R^2$ represents aryl, which can be substituted by halogen, by a radical —A—$R^9$,
in which A represents oxygen, sulphur, SO or SO₂ and $R^9$ represents an optionally substituted aliphatic, aromatic or heterocyclic radical, or by the NO₂ group, or by a dialkylamino group or acylamino group or an alkyl radical which is optionally substituted by halogen or alkoxy, or by optionally substituted aryl, or by a cyano group, a carboxyl group, a carboxylic acid ester group, a carboxylic acid amide group which is optionally substituted on the N atom or a sulphonamide group which is optionally substituted on the N atom, or by a heterocyclic radical which has 5 or 6 ring members and, in addition to carbon, can contain one or more oxygen, sulphur and/or nitrogen atoms, or by a fused-on carbocyclic or heterocyclic ring which has 5 or 6 ring members and, in addition to carbon, can contain one or more oxygen, sulphur and/or nitrogen atoms and further substituents on the carbon and nitrogen atoms, or $R^2$ represents a 4- to 7-membered heterocyclic radical which, in addition to carbon can contain one or more oxygen, sulphur and/or nitrogen atoms and can contain further substituents on the carbon or nitrogen atoms in the ring, such as halogen, $-A-R^9$, with the same meaning for A and $R^9$ as above, an optionally substituted amino group, cyano, a carboxylic acid ester or optionally N-substituted carboxylic acid amide group, optionally substituted alkyl or aryl radicals or further heterocyclic radicals, or can contain fused-on carbocyclic or heterocyclic rings with 5 or 6 ring members, or $R^2$ represents a radical $-O-R^3$, or also represents $S-R^3$ if Y represents CO, in which $R^3$ denotes an alkyl group which has 1 to 12 carbon atoms and can be substituted by halogen or the radical $-A-R^6$, with the same meaning for A and $R^6$ as above, or by nitro, cyano or a carboxylic acid ester group, or by optionally substituted aryl; or $R^3$ furthermore represents an aryl group, which can optionally be substituted by halogen, nitro, cyano, the carboxylic acid ester or optionally N-substituted carboxylic acid amide group or a group $-A-R^9$, with the same meaning for A and $R^9$ as above, or by an alkyl group, which can optionally be substituted by one or more halogen atoms, or by a dialkylamino group or a further aryl radical, or $R^2$ represents a radical

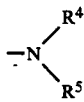

in which $R^4$ denotes hydrogen or an optionally substituted saturated or unsaturated alkyl radical with 1-6 carbon atoms and $R^5$ denotes a saturated or unsaturated alkyl radical which has 1 to 12 carbon atoms and can be substituted by halogen, hydroxyl, acyloxy or the radical $-A-R^6$, with the same meaning for A and $R^6$ as above, or by a group

in which $R^{10}$ and $R^{11}$ each independently denote a hydrogen atom, an alkyl, aryl or heterocyclic radical or an acyl group, or by the cyano group, a carboxylic acid ester radical or a carboxylic acid amide radical which is optionally substituted on the N atom, or by an optionally substituted aryl radical or an optionally substituted or fused heterocyclic radical; or furthermore $R^5$ represents a cycloalkyl radical which has 3 to 8 ring carbon atoms and is optionally substituted by halogen, hydroxyl, alkoxy, aryloxy, alkyl or aryl or optionally contains fused-on rings; or furthermore $R^5$ represents an aryl radical, which can be substituted by halogen, or by a radical $-A-R^9$, in which A represents oxygen, sulphur, SO or $SO_2$ and $R^9$ represents an optionally substituted aliphatic, aromatic or heterocyclic ring, or by the $NO_2$ group, or by a dialkylamino group or acylamino group or an alkyl radical which is optionally substituted by halogen or alkoxy, or by an optionally substituted aryl radical, or by a cyano group, a carboxylic acid ester group, a carboxylic acid amide group which is optionally substituted on the N atom or a sulphonamide group which is optionally substituted on the N atom, or by a heterocyclic radical which has 5 or 6 ring members and, in addition to carbon, can contain one or more oxygen, sulphur and/or nitrogen atoms, or by a fused-on carbocyclic or heterocyclic ring which has 5 or 6 ring members and, in addition to carbon, can contain one or more oxygen, sulphur and/or nitrogen atoms and, on the carbon and nitrogen atoms, further substituents, or $R^5$ furthermore represents a 4- to 7-membered heterocyclic radical which, in addition to carbon, can contain one or more oxygen, sulphur and/or nitrogen atoms and can contain further substituents on the carbon or nitrogen atoms in the ring, such as halogen, $-A-R^9$, with the same meaning for A and $R^9$ as above, an optionally substituted amino group, cyano, a carboxylic acid ester or optionally N-substituted carboxylic acid amide group, optionally substituted alkyl or aryl radicals or further heterocyclic radicals or fused-on carbocyclic or heterocyclic rings with 5 or 6 ring members, or furthermore $R^4$ and $R^5$, together with the nitrogen atom, can form a 3- to 8-membered ring which, in addition to this N atom, can also contain further hetero atoms, which as oxygen, sulphur and nitrogen, and additional substituents and/or fused-on carbocyclic or heterocyclic rings.

Particularly preferred compounds of the formulae (I) and (IA) are those in which R represents hydrogen or alkyl with 1 to 4 carbon atoms, $R^1$ represents fluorine, chlorine, bromine or hydroxyl, or represents alkyl with 1 to 4 carbon atoms, or represents halogenoalkyl with 1 or 2 carbon atoms and 1 to 3 identical or different halogen atoms, or represents alkoxy with 1 to 4 carbon atoms or halogenoalkoxy with 1 or 2 carbon atoms and 1 to 3 identical or different halogen atoms, or represents alkoxyalkoxy with 1 or 2 carbon atoms per alkyl part, or represents alkylthioalkoxy with 1 or 2 carbon atoms per alkyl part, or represents phenoxyalkoxy with 1 or 2 carbon atoms in the alkyl part, or represents alkylthio with 1 to 4 carbon atoms, or represents halogenoalkylthio with 1 or 2 carbon atoms and 1 to 3 identical or different halogen atoms, or represents alkoxyalkylthio with 1 or 2 carbon atoms per alkyl part, or represents alkylthioalkylthio with 1 or 2 carbon atoms per alkyl part, or represents alkylsulphinyl with 1 to 4 carbon atoms, or represents halogenoalkylsulphinyl with 1 or 2 carbon atoms and 1 to 3 identical or different halogen atoms, or represents alkoxyalkylsulphinyl or alkylthioalkylsulphinyl with 1 or 2 carbon atoms per alkyl part, or represents alkylsulphonyl with 1 to 4 carbon atoms, or represents halogenoalkylsulphonyl with 1 or 2 carbon atoms and 1 to 3 identical or different halogen atoms, or represents alkoxyalkylsulphonyl or alkylthioalkylsulphonyl with 1 or 2 carbon atoms per alkyl part, or represents nitro, amino, mono- or dialkylamino with 1 or 2 carbon atoms per alkyl part or acylamino, or represents a fused-on five-membered or six-membered carbocyclic ring which can be interrupted by one or more identical or different atoms from the group comprising oxygen, sulphur and nitrogen atoms, X represents =CH—, or represents a nitrogen atom,
Y represents CO or SO$_2$ and
n represents an integer from 0 to 3, and
R$^2$ represents hydrogen or an alkyl radical which has 1 to 12 carbon atoms and can be substituted by one or more fluorine or chlorine atoms, by a hydroxyl group, by a radical —A—R$^6$,
in which A represents oxygen, sulphur, SO or SO$_2$ and R$^6$ represents an optionally substituted aliphatic, aromatic or heterocyclic radical, or by the NO$_2$ group, or by a group

in which

R$^7$ and R$^8$ denote a hydrogen atom, alkyl with 1 to 4 carbon atoms, phenyl, a 5- or 6-membered heterocyclic radical or an aliphatic, aromatic or heterocyclic acyl group, or by the cyano group, a carboxylic acid ester radical or a carboxylic acid amide radical which is optionally substituted on the N atom by alkyl with 1 to 4 carbon atoms, or by an optionally substituted phenyl radical or an optionally substituted or fused 5- or 6-membered heterocyclic radical, or R$^2$ represents cycloalkyl which has 3 to 6 ring carbon atoms and is optionally substituted by fluorine, chlorine, hydroxyl, alkoxy, phenoxy, alkyl or phenyl or optionally contains fused-on 5- or 6-membered rings, or R$^2$ represents phenyl or naphthyl, which can be substituted by fluorine, chlorine or bromine, or by a radical —A—R$^9$,
in which A represents oxygen, sulphur, SO or SO$_2$ and R$^9$ represents an optionally substituted aliphatic, aromatic or heterocyclic radical, or by the NO$_2$ group, or by a dialkylamino group with 1 or 2 C atoms per alkyl part or acylamino group or an alkyl radical with 1 to 4 carbon atoms which is optionally substituted by halogen or alkoxy, or by an optionally substituted phenyl radical, or by a cyano group, a carboxyl group, a carboxylic acid ester group, a carboxylic acid amide group which is optionally substituted on the N atom by alkyl with 1 to 4 carbon atoms or a sulphonamide group which is optionally substituted on the N atom by alkyl with 1 to 4 carbon atoms, or by a heterocyclic radical which has 5 or 6 ring members and, in addition to carbon, can contain one or more oxygen, sulphur and/or nitrogen atoms, or by a fused-on carbocyclic or heterocyclic ring which has 5 or 6 ring members and, in addition to carbon, can contain one or more oxygen, sulphur and/or nitrogen atoms and, on the carbon and nitrogen atoms, further substituents, or R$^2$ represents a 4- to 7-membered heterocyclic radical which, in addition to carbon, can contain one or more oxygen, sulphur and/or nitrogen atoms and can contain further substituents on the carbon or nitrogen atoms in the ring, such as fluorine, chlorine, —A—R$^9$, with the same meaning for A and R$^9$ as above, an amino group which is optionally substituted by alkyl with 1 to 4 carbon atoms, cyano, a carboxylic acid ester group or a carboxylic acid amide group which is optionally N-substituted by alkyl with 1 to 4 C atoms, optionally substituted alkyl or phenyl radicals or further 5- or 6-membered heterocyclic radicals or can contain fused-on carbocyclic or heterocyclic rings with 5 or 6 ring members, or R$^2$ represents a radical —O—R$^3$, or also represents S—R$^3$, if Y represents CO,
in which R$^3$ denotes alkyl which has 1 to 8 carbon atoms and can be substituted by fluorine, chlorine or the radical —A—R$^6$, with the same meaning for A and R$^6$ as above, or by nitro, cyano or a carboxylic acid ester group, or by optionally substituted phenyl, or R$^3$ represents phenyl, which can optionally be substituted by fluorine, chlorine, bromine, nitro, cyano, carboxylic acid ester group or a carboxylic acid amide group which is optionally N-substituted by alkyl with 1 to 4 carbon atoms, or a group —A—R$^9$, with the same meaning for A and R$^9$ as above, or by an alkyl group with 1 to 4 carbon atoms, which can optionally be substituted by one or more fluorine or chlorine atoms, or by a dialkylamino group with 1 or 2 carbon atoms per alkyl part or a further phenyl radical, or R$^2$ represents

in which

R$^4$ denotes hydrogen or an optionally substituted saturated or unsaturated alkyl radical with up to 4 carbon atoms and R$^5$ denotes a saturated or unsaturated alkyl radical which has 1 to 8 carbon atoms and can be substituted by fluorine, chlorine, hydroxyl, acetoxy or the radical —A—R$^6$, with the same meaning for A and R$^6$ as above, or by a group

in which

R$^{10}$ and R$^{11}$ each independently denote a hydrogen atom, an alkyl, phenyl or 5- or 6-membered heterocyclic radical or an acyl group, or by the cyano group, a carboxylic acid ester radical or a carboxylic acid amide radical which is optionally substituted on the N atom by alkyl with 1 to 4 carbon atoms, or by an optionally substituted phenyl radical or an optionally substituted or fused 5- or 6-membered heterocyclic radical, or R$^5$ furthermore represents cycloalkyl which has 3 to 8 ring carbon atoms and is optionally substituted by fluorine, chlorine, hydroxyl, alkoxy with 1 to 4 carbon atoms, phenoxy, alkyl with 1 to 4 carbon atoms or phenyl or contains optionally fused-on rings, or $R^5$ furthermore represents phenyl, which can be substituted by fluorine, chlorine or bromine, or by a radical —A—$R^9$,
in which A represents oxygen, sulphur, SO or $SO_2$ and $R^9$ represents an optionally substituted aliphatic, aromatic or heterocyclic radical, or by the $NO_2$ group, or by a dialkylamino group with 1 to 4 carbon atoms or an acetylamino group or an alkyl radical which has 1 to 4 C atoms and is optionally substituted by fluorine, chlorine or alkoxy with 1 to 4 C atoms, or by an optionally substituted phenyl radical, or by a cyano group, a carboxylic acid ester group, a carboxylic acid amide group which is optionally substituted on the N atom by alkyl with 1 to 4 carbon atoms or a sulphonamide group which is optionally substituted on the N atom by alkyl with 1 to 4 carbon atoms, or by a heterocyclic radical which has 5 or 6 ring members and, in addition to carbon, can contain one or more oxygen, sulphur and/or nitrogen atoms, or by a fused-on carbocyclic or heterocyclic ring which has 5 or 6 ring members and, in addition to carbon, can contain one or more oxygen, sulphur and/or nitrogen atoms and, on the carbon and nitrogen atoms, further substituents, or $R^5$ furthermore represents a 4- to 7-membered heterocyclic radical which, in addition to carbon, can contain one or more oxygen, sulphur and/or nitrogen atoms and can contain further substituents on the carbon or nitrogen atoms in the ring, such as fluorine, chlorine, —A—$R^9$, with the same meaning for A and $R^9$ as above, an amino group which is optionally substituted by alkyl with 1 to 4 carbon atoms, cyano, a carboxylic acid ester group or a carboxylic acid amide group which is optionally N-substituted by alkyl with 1 to 4 carbon atoms, optionally substituted alkyl or phenyl radicals or further heterocyclic radicals or fused-on carbocyclic or heterocyclic rings with 5 or 6 ring members, or $R^4$ and $R^5$, together with the nitrogen atom, can also form a 3- to 8-membered ring which, in addition to this N atom, can also contain further hetero atoms, such as oxygen, sulphur and nitrogen, and additional substituents and/or fused-on carbocyclic or heterocyclic rings.

Especially preferred compounds of the formulae (I) and (IA) are those
in which

R represents hydrogen, or represents alkyl with 1 to 3 carbon atoms, such as methyl, ethyl, n-propyl and iso-propyl, $R^1$ represents fluorine, chlorine, bromine, hydroxyl, methyl, ethyl, n-propyl, iso-propyl, tert.-butyl, trifluoromethyl, tetrachloroethyl, dichlorofluoromethyl, alkoxy with 1 to 4 carbon atoms, such as methoxy, ethoxy, n- or iso-propoxy, n-butoxy, isobutoxy, sec.-butoxy or tert.-butoxy, trifluoromethoxy, dichlorofluoromethoxy, methoxymethoxy, ethoxymethoxy, 2-methoxyethoxy, 2-ethoxyethoxy, methylthiomethoxy, 2-methylthioethoxy, 2-ethylthioethoxy, phenoxymethoxy, 2-phenoxyethoxy, alkylthio with 1 to 4 carbon atoms, such as methylthio, ethylthio, n- or iso-propylthio, n-butylthio, sec.-butylthio, isobutylthio, tert.-butylthio, trifluoromethylthio, dichlorofluoromethylthio, methoxymethylthio, 2-methoxyethylthio, ethoxymethylthio, 2-ethoxyethylthio, methylthiomethylthio, methylsulphinyl, ethylsulphinyl, trifluoromethylsulphinyl, methoxymethylsulphinyl, methylsulphonyl, ethylsulphonyl, trifluoromethylsulphonyl, methoxymethylsulphonyl, methylthiomethylsulphonyl, nitro, amino, cyano, dimethylamino, diethylamino, monomethylamino, monoethylamino or acetylamino, or represents a fused-on benzene ring or a 5- or 6-membered heterocyclic radical which has 1 or 2 oxygen and/or sulphur and/or nitrogen atoms and is optionally mono-, di-, tri-, tetra- or penta-substituted, such as furan, dioxolene, dioxene, thioxolene, thiophene, pyridine, pyrimidine, oxazole or thiazole, y represents CO or $SO_2$, n represents the integer 0, 1, 2 or 3 and $R^2$ represents hydrogen, or represents saturated or unsaturated alkyl with 1 to 12 carbon atoms or halogenoalkyl with 1 to 4 carbon atoms and 1 to 3 identical or different fluorine, chlorine or bromine atoms, or represents hydroxyalkyl with 1 to 3 carbon atoms, or represents alkoxyalkyl and alkylthioalkyl with in each case 1 to 4 carbon atoms in the alkyl radicals, or represents cycloalkyl which has 3 to 7 carbon atoms and can optionally be mono-, di-, tri- or tetrasubstituted by methyl, or represents phenyl which is optionally mono-, di- or trisubstituted by identical or different substituents from the group comprising alkyl with 1 to 4 carbon atoms, fluorine, chlorine, bromine, nitro, trifluoromethyl, dichlorofluoromethyl, cyano, methoxy, ethoxy, dimethylamino, diethylamino, acetylamino, phenyl, carboxyl, a carboxylic acid amide group or a carboxylic acid ester group, or furthermore represents a 5- or 6-membered heterocyclic radical which can contain 1 to 3 identical or different oxygen, sulphur or nitrogen atoms and can contain fused-on carbocyclic or heterocyclic rings and can optionally be substituted by methyl, ethyl, fluorine, chlorine, cyano, furanyl, substituted amino or carboxyl, for example furan, tetrahydrofuran, thiophene, benzofuran, pyridine, quinoline, imidazole, benzimidazole, pyrimidine, pyridazine, pyrazine, quinazoline, quinoxaline, benzoxazole or benzothiazole, or represents $OR^3$ or also represents $SR^3$, if Y=CO,
wherein $R^3$ represents alkyl with 1 to 6 carbon atoms, halogenoalkyl with 1 to 3 carbon atoms and 1 to 5 identical or different fluorine and chlorine atoms, nitro- or cyanoalkyl with 1 to 4 carbon atoms or phenyl, which is optionally mono-, di- or trisubstituted by identical or different substituents from the group comprising methyl, ethyl, fluorine, chlorine, bromine, $C_1$–$C_4$-alkoxy, $C_1$–$C_4$-dialkylamino, nitro, cyano or a carboxylic acid ester group, or $R^2$ represents

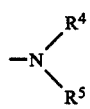

wherein $R^4$ represents hydrogen or alkyl with 1 to 4 carbon atoms and $R^5$ represents hydrogen or alkyl with 1 to 6 carbon atoms, or $R^4$ and $R^5$, together with the nitrogen atom on which they are located, can form a 5- to 7-membered ring which can contain further nitrogen, sulphur or oxygen atoms.

Compounds of the formula (I) or (IA) which may be mentioned in particular are those
in which R represents hydrogen, methyl or ethyl, R¹ represents methoxy, ethoxy, trifluoromethoxy, methyl, ethyl, fluorine, chlorine, bromine, trifluoromethyl, methylthio, ethylthio, trifluoromethylthio, methylenedioxy or nitro, n represents the integer 0, 1 or 2, X represents =CH or a nitrogen atom, Y represents CO or SO₂ and R² represents alkyl with 1 to 4 carbon atoms, such as methyl, ethyl, n-propyl, iso-propyl, n-butyl, iso-butyl, sec.-butyl or tert.-butyl, or represents optionally substituted phenyl, methoxy, ethoxy, phenoxy, furfuryl, dimethylamino or diethylamino, piperidino or morpholino.

If, for example, 1-pyrimid-2-yl-4-phenyl-pyrazolin-5-one and acetic anhydride are used as starting substances, the course of the reaction can be represented by the following equation:

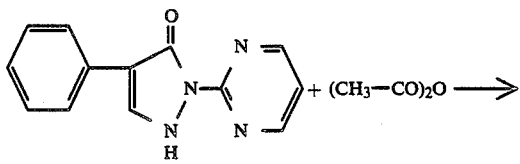

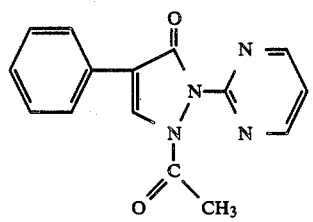

If, for example, 1-pyrid-2-yl-4-phenyl-pyrazolin-5-one, furan-2-carboxylic acid chloride and triethylamine are used as starting substances, the course of the reaction can be represented by the following equation.

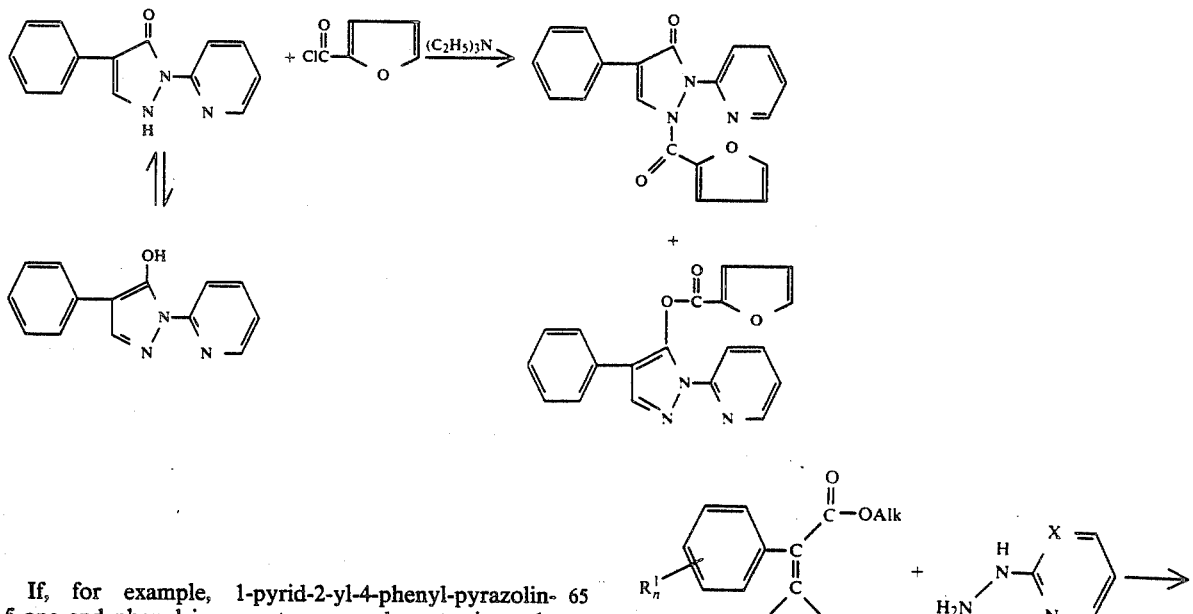

If, for example, 1-pyrid-2-yl-4-phenyl-pyrazolin-5-one and phenyl isocyanate are used as starting substances, the course of the reaction can be represented by the following equation:

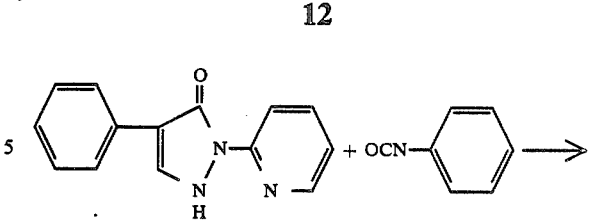

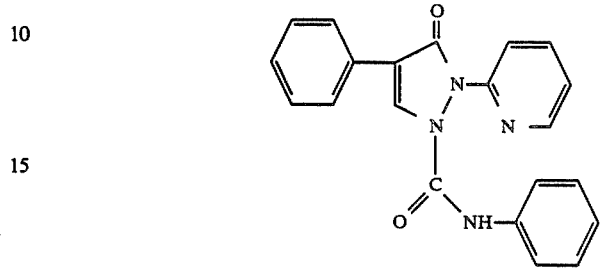

Formula (II) or (IIA) provides a general definition of the 1-pyri(mi)dyl-4-aryl-pyrazolin-5-ones to be used as starting substances in carrying out the process according to the invention. In this formula, R, R¹, X and n have the meaning which has already been mentioned for these symbols in connection with the description of the substances of the formula (I) according to the invention.

The starting substances of the formula (II) or (IIA) and their preparation and use as fungicides are described in application, Ser. No. 733,450, supra.

In accordance with the statements of this patent specification, they are obtained by reaction of α-acyl-phenylacetic acid esters or derivatives thereof of the formula (IV) with 2-hydrazino-pyri(mi)dines (V), which themselves are known from the literature.

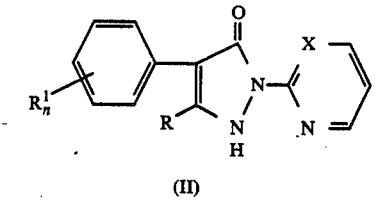

(II)

wherein
W represents OH, OAlk, Hal or NAlk$_2$.

Examples which may be mentioned of starting substances of the formula (II) are: 1-pyrid-2-yl-4-phenyl-pyrazolin-5-one, 1-pyrid-2-yl-4-(4-fluoro-phenyl)-pyrazolin-5-one, 1-pyrid-2-yl-4-(2-chloro-phenyl)-pyrazolin-5-one, 1-pyrid-2-yl-4-(2-bromo-phenyl)-pyrazolin-5-one, 1-pyrid-2-yl-4-(3,4-dichloro-phenyl)-pyrazolin-5-one, 1-pyrid-2-yl-4-(2-methoxy-phenyl)-pyrazolin-5-one,
1-pyrid-2-yl-4-(4-methoxyphenyl)-pyrazolin-5-one, 1-pyrid-2-yl-4-(3-trifluoromethoxyphenyl)-pyrazolin-5-one, 1-pyrid-2-yl-4-(4-trifluoromethylmercapto-phenyl)-pyrazolin-5-one, 1-pyrid-2-yl-4-(4-methyl-phenyl)-pyrazolin-5-one, 1-pyrid-2-yl -4-(3-trifluoromethylphenyl)-pyrazolin-5-one, 1-pyrid-2-yl-3-methyl-4-phenylpyrazolin-5-one, 1-pyrid-2-yl-3-ethyl-4-phenyl-pyrazolin-5-one, 1-pyrimid-2-yl-4-(2-fluoro-phenyl)-pyrazolin-5-one, 1-pyrimid-2-yl-4-(4-chloro-phenyl)-pyrazolin-5-one, 1-pyrimid-2-yl-4-(2-fluoro-6-chloro-phenyl)-pyrazolin-5-one, 1-pyrimid-2-yl-4-(4-methoxy-phenyl)-pyrazolin -5-one, 1-pyrimid-2-yl-4-(3,4-difluoromethylenedioxy-phenyl)-pyrazolin-5-one, 1-pyrimid-2-yl-4-(2-methoxy-phenyl)-pyrazolin-5-one, 1-pyrimid-2-yl-4-(2-chloro-5-trifluoromethyl-phenyl)-pyrazolin-5-one and 1-pyrimid-2-yl-3-methyl-4-phenyl-pyrazolin-5-one.

The acid derivatives of the formula (III) also to be used as starting substances for the preparation of the compounds according to the invention are known. They are the reactive derivatives, customary for acylation reactions, of carboxylic acids, carbonic acid esters, carbamic acids, sulphonic acids and sulphamic acids, in particular carboxylic acid halides, carboxylic acid anhydrides, mixed anhydrides of carboxylic acids and carbonic acid esters, carboxylic acid azolides, ketenes, carbonic acid ester-halides, dicarbonic acid esters, carbamic acid halides, isocyanates, sulphonic acid halides, sulphonic acid anhydrides and the like.

The reaction of the 1-pyri(mi)dyl-4-aryl-pyrazolin-5-ones of the formula (II) or (IIA) with the reactive derivatives of carboxylic acids, carbonic acid esters, carbamic acids, sulphonic acids, or sulphamic acids of the formula (III) is carried out under the conditions known in principle for acylation reactions.

If carboxylic acid anhydrides, mixed anhydrides of carboxylic acids and carbonic acid esters, dicarbonic acid dialkyl esters or sulphonic acid anhydrides are used as the acylating component, this acylation can be carried out without further auxiliaries, by allowing the reaction components to act on one another, preferably in an equimolar ratio, in undiluted form or in diluents. However, it may also be advantageous to employ the acylating agent in an excess of up to a further mole or, as in the case of carboxylic acid anhydrides, to use this as the solvent in a larger excess.

The reactions are advantageously carried out in diluents, it being possible to use all the solvents which are inert towards the reaction partners. These include hydrocarbons, such as benzine or toluene, halogenohydrocarbons, such as methylene chloride, chloroform and carbon tetrachloride, ketones, such as acetone or methyl isopropyl ketone, ethers, such as diethyl ether, tetrahydrofuran or dioxane, and furthermore dimethylsulphoxide, tetrahydrothiophene dioxide and dimethylformamide.

The reaction temperatures can be varied within a substantial range. The reaction is in general carried out between −20° C. and 150° C., preferably between room temperature and the boiling point of the solvent used.

If carboxylic acid halides, carbonic acid ester-halides, carbamic acid halides or sulphonic acid halides are employed as the acylating component, it is advantageous to add an auxiliary base to bond the hydrogen halides liberated during the reaction. Suitable auxiliary bases are: alkali metal and alkaline earth metal hydroxides and carbonates and tertiary amines, such as, for example, triethylamine, pyridine and N,N-dimethyl-aniline.

The acylating agent and the acid-binding base are preferably employed in each case in equimolar amounts in relation to the reaction component of the formula (II) or (IIA), but it may be advantageous to employ either only the auxiliary base or the acylating component and the auxiliary base in an excess of up to a further mole.

An alternative in the reaction procedure comprises initially converting the pyrazolinone of the formula (II) or (IIA) into a metal salt in an inert solvent and then reacting this salt with the acylating agent. This can be effected, for example, with strong bases, such as sodium hydride, sodium or potassium amide or potassium tert.-butylate.

The reactions are preferably carried out in inert solvents, those already mentioned above being suitable. The reaction temperatures are −20° C. to 150° C., preferably 0° to 100° C.

If isocyanates are employed as the acylating component, the reaction is as a rule carried out with an equimolar amount of the reaction components in the above-mentioned solvents. The reaction temperatures are 0° to 100° C. Activators, such as, for example, 1,4-diazabicyclooctane (DABCO) and tin-II octoate, can be used to accelerate the reaction.

The reaction products are isolated in the customary manner by distilling off the solvent and, thoroughly washing the amine hydrochloride which may be formed in the reaction, or by precipitation with water in the case where the reaction is carried out in a water-miscible solvent.

The active compounds according to the invention exhibit a powerful microbicidal action and can be employed in practice for combating undesired microorganisms. The active compounds are suitable for use as plant protection agents, in particular as fungicides or can be used in the preservation of materials for the preservation of industrial materials.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are used in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv.oryzal; Pseudomonas species, such as, for example, *Pseudomonas oyringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for exmaple, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds; and of the soil.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mine al oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable; for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and as mixtures with fertilizers and growth regulators.

The active compounds can be used as such, in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds of the formula (I) according to the invention show good actions against causative organisms of cereal diseases, against causative organisms of rice diseases (*Pyricularia oryzae*) and against causative organisms of vegetable and fruit diseases (*Botrytis cinerea*). When used accordingly, the compounds likewise also have a bactericidal action, and they also show an action in the plate test.

According to the invention, industrial materials are non-living materials which have been prepared for use in industry. Industrial materials which are to be preserved by active compounds according to the invention from microbial change or destruction can be, for example, adhesives, sizes, paper and card, textiles, leather, wood, paints and articles made of plastic, cooling lubricants and other materials which can be attacked or decomposed by microorganisms. Components of production plants, for example cooling water circulations, which can be impaired by multiplication of microorganisms may also be mentioned in the context of materials to be preserved. Adhesives, sizes, paper and card, leather, wood, paints, cooling lubricants and cooling circulations may be mentioned as preferred industrial materials in the context of the present invention.

Examples which may be mentioned of microorganisms which can cause degradation of or a change in the industrial materials are bacteria, fungi, yeasts, algae and slime organisms. The active compounds according to the invention act preferentially against fungi, in particular moulds, fungi which discolor wood and destroy wood (Basidiomycetes) and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa* and Staphylococcus, such as *Staphylococcus aureus*.

An active compound according to the invention can be converted into the customary formulations according to the field of use, such as solutions, emulsions, suspensions, powders, pastes and granules.

These can be prepared in a manner which is known per se, for example by mixing the active compounds with an extender consisting of liquid solvent and/or solid excipients, if appropriate using surface-active agents, such as emulsifiers and/or dispersing agents, and, in the case of the use of water as an extender, organic solvents, such as alcohols, can, if appropriate, be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, or halogenated hydrocarbons, such as 1,2-dichloroethane.

Microbicidal agents in general contain the active compounds in an amount of 1 to 95%, preferably 10 to 75%.

The use concentrations of the active compounds according to the invention depend on the nature and occurrence of the microorganisms to be combated and on the composition of the material to be preserved. The optimum amount to be used can be determined by test series. The use concentrations are in general in the range from 0.001 to 5% by weight, preferably 0.05 to 1.0% by weight, based on the material to be preserved.

The active compounds according to the invention can also be present as a mixture with other known active compounds. The following active compounds may be mentioned as examples: benzyl alcohol mono(poly)-hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, 2-thiocyanatomethylthiobenzothiazole, organo-tin compounds, methylenebisthiocyanate and phenol derivatives, such as 2-phenylphenol, (2,2'-dihydroxy-5,5'-dichloro)diphenylmethane and 3-methyl-4-chlorophenol.

PREPARATION EXAMPLES

Example 1

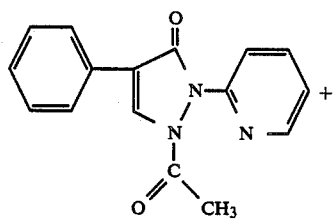

+

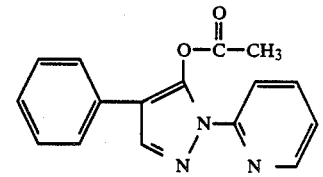

23.7 g (0.1 mole) of 1-pyrid-2-yl-4-phenyl-pyrazolin-5-one are boiled under reflux in 150 ml of acetic anhydride for 6 hours. Excess acetic anhydride and the acetic acid formed are distilled off in vacuo. The residue which remains is dissolved in 100 ml of ethyl acetate and the solution is cooled in ice for several hours. The crystals which have separated out are filtered off with suction and dried.

20.4 g (73% of theory) of a mixture of 1-pyrid-2-yl-2-acetyl-4-phenyl-pyrazolin-5-one and 1-pyrid-2-yl-4-phenyl-5-acetoxypyrazole in a ratio of 60:40 (according to the $^1$H-proton resonance spectrum) of melting point: 158°–162° C. are obtained.

The following compounds are obtained in an analogous manner:

Example 2

1-Pyrimid-2-yl-2-acetyl-4-phenyl-pyrazol-5-one
Melting point: 171°–173° C. (from ethyl acetate).

Example 3

1-Pyrimid-2-yl-2-acetyl-3-methyl-4-phenyl-pyrazol-5-one
Melting point: 138°–140° C. (from toluene).

According to the $^1$H-proton resonance spectrum, the compounds according to Examples 2 and 3 are single compounds and, according to the $^{13}$C nuclear magnetic resonance spectrum, contain the acetyl radical in the 2-position.

Example 4

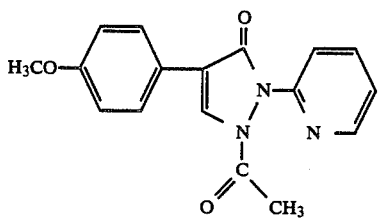

26.7 g (0.1 mole) of 1-pyrid-2-yl-4-(4-methoxy-phenyl)-pyrazolin-5-one are dissolved in 200 ml of dioxane. 10.1 g (0.1 mole) of triethylamine and 0.2 g of 4-dimethylaminopyridine are added and 7.9 g (0.1 mole) of acetyl chloride are then added dropwise at room temperature. The mixture is subsequently stirred at room temperature for a further hour and at 90° C. for 3 hours, cooled and stirred into 1 l of water. The crystals which have separated out are filtered off with suction, dried in air and recrystallized from cleaner's naptha. 20.7 g (67% of theory) of 1-pyrid-2-yl-2-acetyl-4-(4-methoxy-phenyl)-pyrazolin-5-one of melting point 98°–100° C., which is contaminated only by a little 5-acetoxy derivative, are obtained.

The following compounds are obtained in an analogous manner:

| Example | X | R¹ | n | R² | R | Melting point (°C.) | Recrystallized from |
|---|---|---|---|---|---|---|---|
| 5 a | N | — | 0 | —C(CH₃)₃ | H | 140–141 | Toluene |
| 6 a | CH | — | 0 | phenyl | H | 114–116 | Cleaner's naphtha |
| 7 a | CH | 4-OCH₃ | 1 | phenyl | H | 156–157 | Toluene |
| 8 a | CH | — | 0 | furyl | CH₃ | 115–117 | Cleaner's naphtha |
| 9 a | N | — | 0 | furyl | H | 221–223 | Butanol |
| 10 a | CH | — | 0 | —O—CH₃ | CH₃ | 150–152 | Cleaner's naphtha |
| 11 a | N | — | 0 | —O—CH₃ | H | 174 | Toluene |
| 12 a | N | — | 0 | —O—phenyl | H | 162–164 | Toluene/ligroin |
| 13 a | N | 2-CH₃ | 1 | phenyl | H | 128.5 | Ethanol |
| 14 a | CH | 2-CH₃ | 1 | phenyl | H | 88–89 | Diisopropyl ether |
| 15 a | CH | 2-CH₃ | 1 | furyl | H | 102–104 | Diisopropyl ether |

-continued

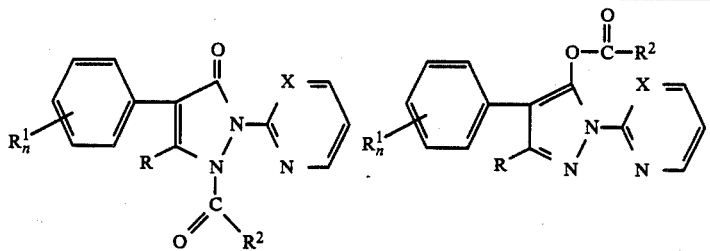

| Example | X | R¹ | n | R² | R | Melting point (°C.) | Recrystallized from |
|---|---|---|---|---|---|---|---|
| 16 a | CH | 2-Cl, 6-F | 2 | phenyl | H | 121–122 | Toluene |
| 17 a | N | 2-Cl, 6-F | 2 | phenyl | H | 116–118 | Diisopropyl ether |
| 18 a | CH | — | 0 | 4-CF₃-phenyl | H | 77–79 | Cleaner's naphtha |
| 19 a | CH | — | 0 | 4-NO₂-phenyl | H | 212–214 | Toluene |
| 20 a | CH | 3-Cl | 1 | phenyl | H | 88–90 | Cleaner's naphtha |
| 21 a | CH | 4-CH₃ | 1 | phenyl | H | 114–116 | Cleaner's naphtha |
| 22 a | CH | 4-CF₃ | 1 | phenyl | H | 132–134 | Cleaner's naphtha |
| 23 a | CH | 4-Cl | 1 | phenyl | H | 134–136 | Cleaner's naphtha |
| 23 b | CH | 2-Cl, 6-F | 2 | furyl | H | 107–109 | Diisopropyl ether |
| 23 c | N | — | 0 | 4-OCH₃-phenyl | H | 159–160 | Carbontetrachloride |
| 23 d | N | 3-CH₃ | 1 | phenyl | H | 126–128 | Cleaner's naphtha |

-continued

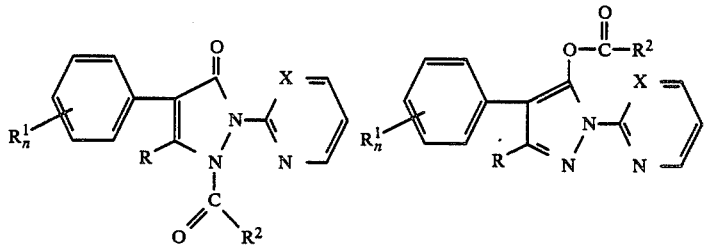

| Example | X | R¹ | n | R² | R | Melting point (°C.) | Recrystallized from |
|---|---|---|---|---|---|---|---|
| 23 e | CH | 4-Cl | 1 | (2-furyl) | H | 115–117 | Carbontetrachloride |
| 23 f | N | 4-OCH₃ | 1 | (phenyl) | H | 124–125 | Carbontetrachloride |

Example 24

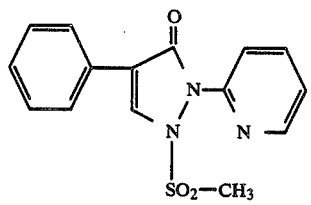

23.7 g (0.1 mole) of 1-pyrid-2-yl-4-phenyl-pyrazolin-5-one are dissolved in 200 ml of dioxane. After addition of 10.1 g (0.1 mole) of triethylamine, 11.5 g (0.1 mole) of methanesulphonyl chloride are added dropwise at room temperature, while cooling gently. The mixture is subsequently stirred at room temperature for a further 2 hours and at 70° C. for 5 hours, cooled and stirred into 1 l of water. The crystals are filtered off with suction, dried in air and recrystallized from ethanol. 22.5 g (71% of theory) of 1-pyrid-2-yl-2-methylsulphonyl-4-phenyl-pyrazolin-5-one of melting point 112°–114° C. are obtained.

The following compounds are obtained in an analogous manner:

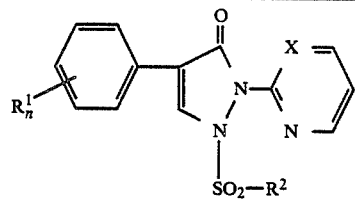

| Example | X | R¹ | n | R² | R | Melting point (°C.) | Recrystallized from |
|---|---|---|---|---|---|---|---|
| 25 | CH | — | 0 | (phenyl) | | 132–134 | Toluene |
| 26 | CH | 4-OCH₃ | 1 | (phenyl) | | 133–135 | Toluene |
| 27 | CH | — | 0 | —N(CH₃)₂ | | 135–137 | Toluene |
| 28 | N | — | 0 | —N(CH₃)₂ | | 166–168 | Toluene |
| 29 | CH | 2-Cl | 1 | (phenyl) | H | 135 | Ethanol |

-continued

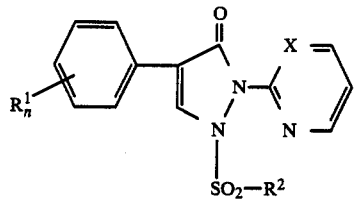

| Example | X | R$^1$ | n | R$^2$ | R | Melting point (°C.) | Recrystallized from |
|---|---|---|---|---|---|---|---|
| 30 | CH | 2-Cl, 6-F | 2 | phenyl | H | 128–130 | Diisopropyl ether |
| 31 | N | 2-Cl, 6-F | 2 | phenyl | H | 198–200 | Butanol |
| 32 | CH | 2-CH$_3$ | 1 | phenyl | H | 119–121 | Cleaner's naphtha |
| 33 | CH | 3-Cl | 1 | phenyl | H | 124–126 | Cleaner's naphtha |
| 34 | CH | 4-CH$_3$ | 1 | phenyl | H | 132–134 | Toluene |
| 35 | CH | 4-CF$_3$ | 1 | phenyl | H | 159–161 | Toluene |
| 36 | CH | 4-Cl | 1 | phenyl | H | 138–140 | Butanol |

USE EXAMPLES

The compound shown below is employed as the comparison substance in the use examples which follow:

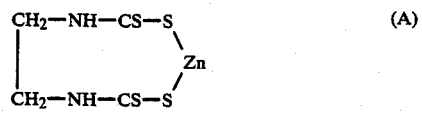 (A)

Example A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 1, 2, 9a and 24.

Example B

The minimum inhibitory concentrations (MIC) of active compounds according to the invention are determined to demonstrate the activity against fungi:

Active compounds according to the invention are added in concentrations of 0.1 mg/l to 5,000 mg/l to an agar prepared from beer wort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which the species of microbe used shows no growth at all. Good actions of the listed test organisms are shown, for example, by the compounds according to Preparation Examples 2, 6a, 12a, 9b, 24 and 25:

Alternaria tenuis
Aspergillus niger
Aureobasidium pullulans
Chaetomium globosum
Cladosporium cladoporioides
Lentinus tigrinus
Penicillium glaucum
Polyporus versicolor
Sclerophoma pityophila Example C Action against bacteria Active compounds according to the invention are added in concentrations of 1 to 5,000 ppm to an agar containing broth as a nutrient medium. The nutrient medium is then infected with in each case the test organisms listed in Table C and the infected medium is kept at 28° C. and 60 to 70% relative atmospheric humidity for 2 weeks. The MIC is the lowest concentration of active compound at which the species of microbe used shows no growth at all. The compounds according to Preparation Examples 2, 6a, 12a, 9b, 13 and 14 show good actions.

TABLE C

MIC values in mg/l on action of the active compounds shown below on bacteria.

| Test organisms | MIC in mg/l of the active compounds Example No. | | | | | |
|---|---|---|---|---|---|---|
| | 2 | 6a | 12a | 9b | 24 | 25 |
| Escherichia coli | 750 | 350 | 200 | 200 | 50 | 1,000 |
| Staphylococcus aureus | 1,000 | 100 | 500 | 500 | 50 | 20 |

Example D

Action against slime organisms

Substances according to the invention are used in concentrations of in each case 0.1 to 100 mg/l in Allen's nutrient solution (Arch. Mikrobiol. 17, 34 to 53 (1952)), which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, dissolved in a little acetone. Shortly beforehand, the nutrient solution is infected with slime organisms (about $10^6$ germs/ml) which have been isolated from spinning water circulations used in polyamide production. Nutrient solutions which contain the minimum inhibitory concentration (MIC) or larger concentration of active compound are still completely clear after culture at room temperature for 3 weeks, i.e. the pronounced multiplication of the microbes and slime formation noticeable after 3 to 4 days in nutrient solutions containing no active compound is absent. A good action is shown by the compound according to Preparation Example 13.

TABLE D

| MIC value in mg/l on action of the substance shown below on slime organisms | |
|---|---|
| Active compound | MIC in mg/l |
| Example No. 24 | 2–<5 |

It is understood that the specification and examples are illustrative but not limitative of the present invention and that other embodiments within the spirit and scope of the invention will suggest themselves to those skilled in the art.

We claim:

1. A 1-heteroaryl-4-aryl-pyrazole derivative of the formula (I) or (IA)

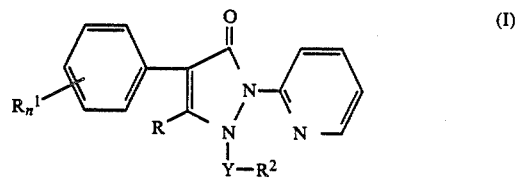

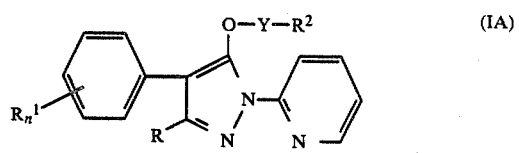

in which

R represents hydrogen or represents alkyl with 1 to 3 carbon atoms, $R^1$ represents fluorine, chlorine, bromine, hydroxyl, methyl, ethyl, n-propyl, iso-propyl, tert.-butyl, trifluoromethyl, tetrachloroethyl, dichlorofluoromethyl, alkoxy with 1 to 4 carbon atoms, trifluoromethoxy, dichlorofluoromethoxy, methoxymethoxy, ethoxymethoxy, 2-methoxyethoxy, 2-ethoxyethoxy, methylthiomethoxy, 2-methylthioethoxy, 2-ethylthioethoxy, phenoxymethoxy, 2-phenoxyethoxy, alkylthio with 1 to 4 carbon atoms, trifluoromethylthio, dichlorofluoromethylthio, methoxymethylthio, 2-methoxyethylthio, ethoxymethylthio, 2-ethoxyethylthio, methylthiomethylthio, methylsulphinyl, ethylsulphinyl, trifluoromethylsulphinyl, methoxymethylsulphinyl, methylsulphonyl, ethylsulphonyl, trifluoromethylsulphonyl, methoxymethylsulphonyl, methylthiomethylsulphonyl, nitro, amino, cyano, dimethylamino, diethylamino, monomethylamino, monoethylamino or acetylamino, or represents a fused-on benzene ring or a furan, dioxolene, dioxene, thioxolene, thiophene, pyridine, oxazole or thiazole radical, Y represents CO or $SO_2$, n represents an integer from 0 to 5 and $R^2$ represents hydrogen or represents alkyl or alkenyl with 1 to 12 carbon atoms or halogenoalkyl with 1 to 4 carbon atoms and 1 to 3 identical or different fluorine, bromine, or chlorine atoms, or represents hydroxyalkyl with 1 to 3 carbon atoms, or represents alkoxyalkyl or alkylthioalkyl with in each case 1 to 4 carbon atoms in the alkyl radicals, or represents cycloalkyl which has 3 to 7 carbon atoms and can optionally be mono-, di-, tri- or tetrasubstituted by methyl, or represents phenyl which is optionally mono-, di- or trisubstituted by identical or different substituents from the group consisting of alkyl with 1 to 4 carbon atoms, fluorine, chlorine, bromine, nitro, trifluoromethyl, dichlorofluoromethyl, cyano, methoxy, ethoxy, dimethylamino, diethylamino, acetylamino, phenyl, carboxyl or a carboxylic acid amide group, or furthermore represents a furan, tetrahydrofuran, thiophene, benzofuran, pyridine, quinoline, imidazole, benzimidazole, benzoxazole or benzothiazole radical and can optionally be substituted by methyl, ethyl, fluorine, chlorine, cyano, phenyl, an unsubstituted amino or amino substituted by $C_1-C_4$-alkyl or cyano or carboxyl, or represents $OR^3$ or also represents $SR^3$, if $Y=CO$, wherein $R^3$ represents alkyl with 1 to 6 carbon atoms, halogenoalkyl with 1 to 3 carbon atoms and 1 to 5 identical or different fluorine and chlorine atoms, nitro- or cyanoalkyl with 1 to 4 carbon atoms in the alkyl part or phenyl, which is optionally mono-, di- or trisubstituted by identical or different substituents from the group consisting of methyl, ethyl, fluorine, chlorine, bromine, $C_1-C_4$-alkoxy, $C_1-C_4$-dialkylamino, nitro or cyano group, or $R^2$ represents

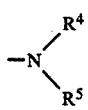

wherein $R^4$ represents hydrogen or alkyl with 1 to 4 carbon atoms and $R^5$ represents hydrogen or alkyl with 1 to 6 carbon atoms, or $R^4$ and $R^5$ together with the nitrogen atom on which they are located, form a piperidino or morpholino ring.

2. A 1-heteroaryl-4-aryl-pyrazole derivative according to claim 1, wherein

R represents hydrogen, methyl or ethyl, $R^1$ represents methoxy, ethoxy, trifluoromethoxy, methyl, ethyl, fluorine, chlorine, bromine, trifluoromethyl, methylthio, ethylthio, trifluoromethylthio, methylenedioxy or nitro, n represents the integer 0, 1 or 2, Y represents CO or $SO_2$ and $R^2$ represents alkyl with 1 to 4 carbon atoms or represents optionally substituted phenyl, methoxy, ethoxy, phenoxy, furfuryl, dimethylamino or diethylamino, piperidino or morpholino.

3. A compound according to claim 1 wherein such compound is 1-pyrid-2-yl-2-acetyl-4-phenyl-pyrazolin-5-one of the formula

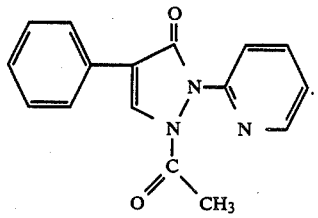

4. A compound according to claim 1 wherein such compound is 1-pyrid-2-yl-4-phenyl-5-acetoxypyrazole of the formula

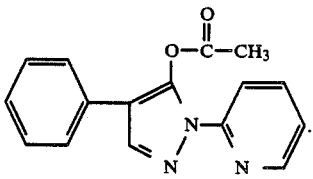

5. A microbicidal composition comprising a microbicidally effective amount of a compound according to claim 1 in admixture with a diluent.

6. A method of combating microorganisms which comprises applying to such microorganisms or a habitat thereof a microbicidally effective amount of a compound according to claim 1.

7. A method according to claim 6, wherein such compound is 1-pyrid-2-yl-2-acetyl-4-phenyl-pyrazolin-5-one, or 1-pyrid-2-yl-4-phenyl-5-acetoxypyrazole.

* * * * *